United States Patent
Baliga et al.

[19]

[11] Patent Number: 5,936,250
[45] Date of Patent: Aug. 10, 1999

[54] ULTRAVIOLET TOXIC GAS POINT DETECTOR

[75] Inventors: Shankar Baliga, Irvine; Herbert H. Rabe, Laguna Beach, both of Calif.

[73] Assignee: General Monitors, Incorporated, Lake Forest, Calif.

[21] Appl. No.: 08/899,516

[22] Filed: Jul. 24, 1997

[51] Int. Cl.⁶ .................................................. G01N 21/33
[52] U.S. Cl. ........................................ 250/373; 250/345
[58] Field of Search .................................. 250/372, 373, 250/338.5, 339.13, 345

[56] References Cited

U.S. PATENT DOCUMENTS

| | | |
|---|---|---|
| 3,795,812 | 3/1974 | Okabe . |
| 3,809,905 | 5/1974 | Suga ........................................ 250/372 |
| 3,906,226 | 9/1975 | Okabe et al. . |
| 3,982,130 | 9/1976 | Trumble . |
| 4,411,867 | 10/1983 | Ostrander . |
| 4,591,721 | 5/1986 | Wong ...................................... 250/373 |
| 4,775,794 | 10/1988 | Behmann . |
| 4,844,611 | 7/1989 | Imahashi et al. . |
| 5,163,332 | 11/1992 | Wong ................................. 250/338.5 |
| 5,222,389 | 6/1993 | Wong .................................... 73/31.02 |
| 5,281,816 | 1/1994 | Jacobson et al. . |
| 5,332,901 | 7/1994 | Eckles et al. ........................... 250/345 |
| 5,341,214 | 8/1994 | Wong ................................. 250/338.5 |
| 5,379,026 | 1/1995 | Whittle . |
| 5,475,222 | 12/1995 | King ................................... 250/338.5 |
| 5,512,757 | 4/1996 | Cederstrand et al. .................. 250/373 |
| 5,567,945 | 10/1996 | Drevline et al. ........................ 250/373 |
| 5,608,219 | 3/1997 | Aucremanne . |

FOREIGN PATENT DOCUMENTS 0 773 435 A2 7/1996 European Pat. Off. .
0 773 435 A3 7/1996 European Pat. Off. .

OTHER PUBLICATIONS

Patent Abstracts of Japan vol. 096, No. 006, Jun. 28, 1996 & JP 08 043302 A (Horibaltd).

Primary Examiner—Constantine Hannaher
Assistant Examiner—Darren M. Jiron
Attorney, Agent, or Firm—Larry K. Roberts

[57] ABSTRACT

Apparatus for the optical detection of selected toxic gases, using the ultraviolet region of the electromagnetic spectrum, and the known absorption properties of the toxic gases in the ultraviolet region. An ultraviolet flashlamp source illuminates a straight, highly polished metal tube with numerous perforations to permit access for the gas to be detected. The ultraviolet light then enters an optical compartment comprising an optical beamsplitter and two ultraviolet detectors with wavelength selective narrowband filters attached. The filters are selected so that one overlaps the region of absorption by the gas while the second is in a region where there is no absorption by the gas. The electronic circuit following the ultraviolet detectors and the drivers for the flashlamp, are timed by a microprocessor that provides the means for the electronics and data processing to be synchronized with the flashlamp pulse. The concentration of the absorbing gas is calculated from the output of the two detectors including the dark outputs measured while the flashlamp is turned off. By this method a parts per million sensitive toxic gas sensor useful to measure gases such as hydrogen sulfide, sulfur dioxide and benzene is obtained.

29 Claims, 3 Drawing Sheets

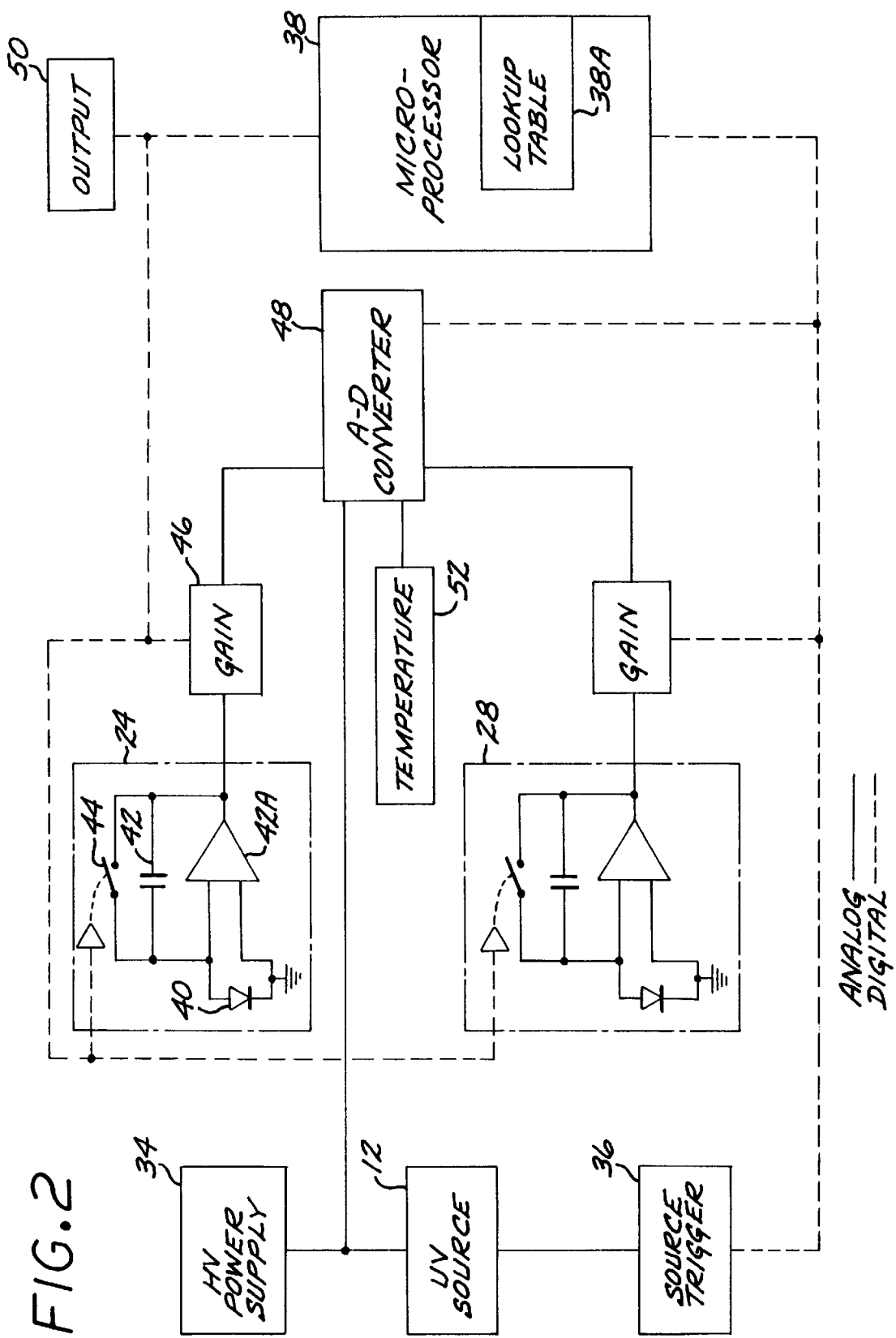

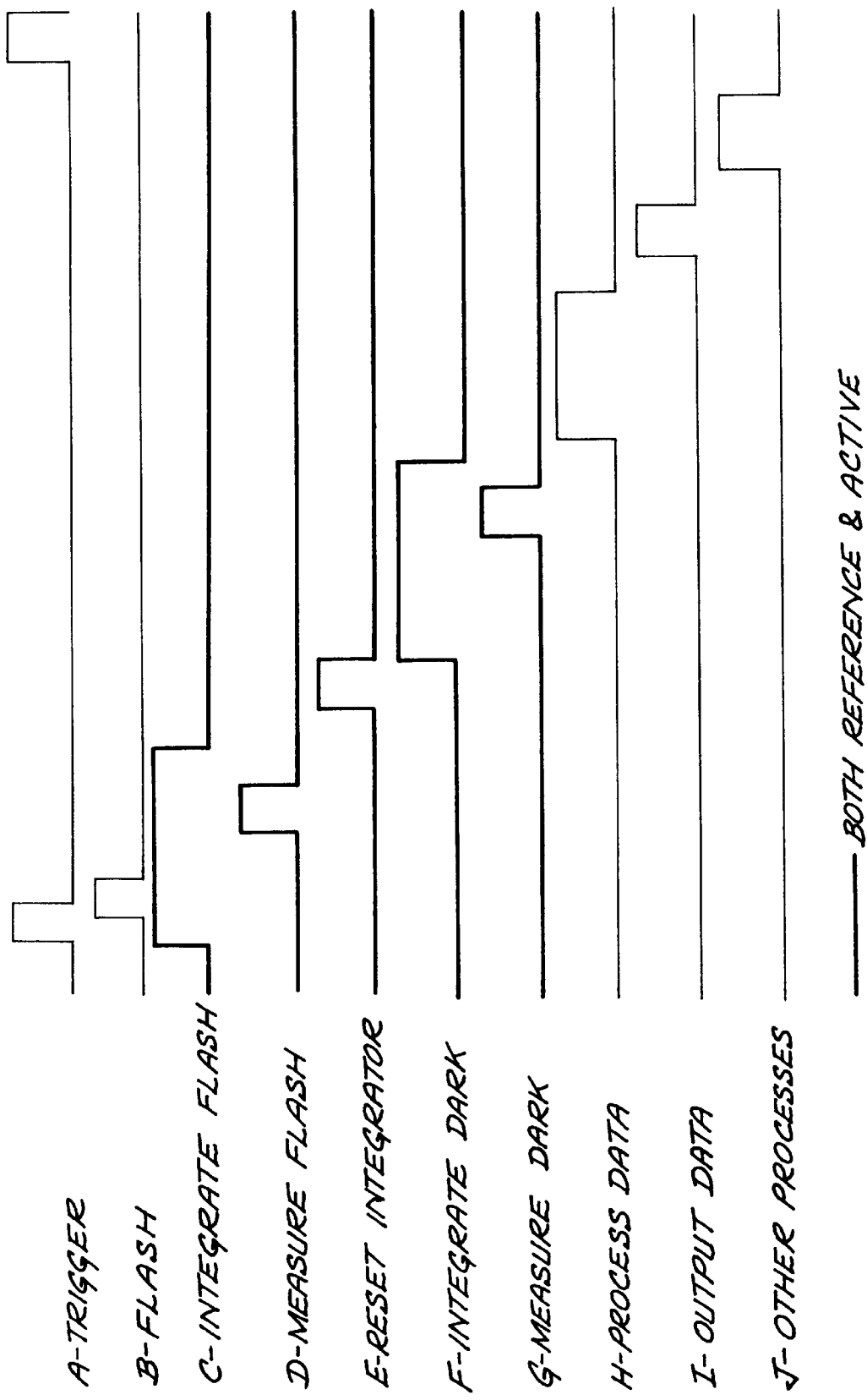

ULTRAVIOLET TOXIC GAS POINT DETECTOR

TECHNICAL FIELD OF THE INVENTION

This invention relates to optical gas detectors used to detect small quantities of gases by their characteristic absorption in specific parts of the electromagnetic spectrum. More particularly, it relates to an apparatus to monitor the presence of unsafe levels of toxic gases such as $H_2S$, $SO_2$ and $C_6H_6$ in a fixed location by studying their ultraviolet absorption behavior.

BACKGROUND OF THE INVENTION

Gas detectors which operate and monitor gas concentrations in a fixed location are known in the industry as point detectors. Point gas detectors have traditionally employed catalytic beads, electrochemical cells and other chemical sensors such as MOS sensors depending on gas type and concentration. These types of sensors suffer from various drawbacks such as poisoning by other chemicals, the need for oxygen to function, limited operating temperatures, drift with time and the requirement for periodic field calibration. Another major drawback is that the sensors are not fail-to-safe, i.e. they do not inform the user when they are dysfunctional.

In recent years, optical based gas sensors have been introduced in the marketplace with the bulk of products utilizing infrared wavelengths to measure gases such as hydrocarbons, carbon dioxide and carbon monoxide. The infrared region is a preferred region since these gases have strong absorption due to fundamental vibrational-rotational bands as at 3.3 microns for methane and 4.2 microns for carbon dioxide. In optical gas sensors signals are present at all concentrations of gas including zero gas. As a result, it is easy to detect a fault in the system leading to the fail-to-safe operation. In contrast, catalytic sensors tend to simply lose their sensitivity when poisoned without the knowledge of the user.

Toxic gases such as hydrogen sulfide and sulfur dioxide occur in nature accompanying natural gas, and are also used extensively in the chemical industry. Unlike hydrocarbons which are combustible and need to be measured in LEL's (lower explosive limit) of a few percent by volume, toxic gases are unsafe for humans to breathe in much smaller doses typically of parts per million (ppm). Hence, these gases need to be measured in parts per million, and sometimes as with benzene in sub-ppm or parts per billion (ppb) concentrations. Detailed laboratory studies have shown that most of these toxic gases have very weak absorption in the infrared which, combined with the requirement of parts per million detection, make gas detectors operating in the infrared unsuited to these gases.

Studies in another part of the electromagnetic spectrum, namely the ultraviolet region, have shown that many toxic gases are strongly absorbing in the ultraviolet (uv). The region from 190 to 230 nanometers (nm) is strongly absorbing for hydrogen sulfide, sulfur dioxide, and the aromatics benzene, toluene and xylene. Below 190 nm the atmosphere strongly absorbs the deep ultraviolet radiation; the region below 190 nm is therefore known as the vacuum ultraviolet (vuv) region. Though ultraviolet based instruments are used in the process industry in flow measurements of toxic gases, no human and animal point safety product based on ultraviolet absorption principles is known to exist in the marketplace. U.S. Pat. No. 3,795,812 issued Mar. 5, 1974 and U.S. Pat. No. 3,906,226 issued Sept. 16, 1975 describe ultraviolet fluorescence monitors used to measure and control the emission of sulfur dioxide and nitric oxide respectively. Fluorescence monitoring is based on the efficient re-emission of radiation when these compounds are excited by light, and is a different technique from a non-dispersive absorption technique in accordance with this invention.

It would therefore represent an advance in the art to provide an optical absorption instrument utilizing absorption in the 190 to 230 nm region as an active indicator of gas, and using a second wavelength centered at 280 nm where the toxic gases are not absorbing as a reference channel.

SUMMARY OF THE INVENTION

The present invention includes a gas filled flashlamp source with an ultraviolet transmitting window such as magnesium fluoride or silica. The ultraviolet radiation then passes into a metal tube several inches long and of a diameter corresponding to the ultraviolet window of the flashlamp. This tube is made of metal such as aluminum and is highly polished on its inside. The tube thereby acts as a light guide and collimates the uv radiation from the flashlamp. Experiments with unpolished tubes and with tubes of different materials, surface finishes and coatings have shown that both the degree of polish and the coating on the tube, if any, are important to propagation of the ultraviolet radiation. A high degree of mechanical polish of aluminum gives excellent optical transmission via multiple reflections, whereas coating the polished aluminum with nickel is more suitable for corrosive environments. The tube has several holes or slots placed along its length so as to permit free access of the absorbing gas. The size and number of perforations is selected to provide the desired response time of a few seconds of the gas sensor. The length of the tube determines the sensitivity of the instrument; a longer tube provides a longer pathlength and, per Beer-Lambert's Law, more sensitivity. A tube length of several inches has been found adequate to measure parts per million of hydrogen sulfide.

The flashlamp is a short arc xenon flashlamp which provides microsecond duration, high intensity pulses of light of a continuous spectrum from the ultraviolet to the infrared. This type of flashlamp is known for good arc stability, low jitter, and long life measured in billions of pulses which corresponds to several years of operation.

After traversing the gas absorption tube, the uv radiation then passes through a focusing lens onto a beamsplitter that selectively separates the active and reference wavelengths, one by reflection and the other by transmission. The radiation is received and detected by a pair of uv-enhanced silicon photodiodes which have narrowband, filters corresponding to the active and reference wavelengths, attached in front of them or installed into the cover of the detector TO package itself. (TO-style packages are industry standard electronic packages, TO-5 having a diameter of 0.36 inch.) Typical filter center wavelengths and the pass bands used are 198 nm +/−10 nm for the active and 280 nm +/−10 nm for the reference. Other filter center wavelengths and pass bands in the ultraviolet may be used depending on the gas and the concentration, within the scope of this invention.

The duration of the flashlamp pulse is a few microseconds. A high speed integrator is connected to each uv photodetector to integrate the current generated. Integration is achieved by means of a capacitor in the feedback loop of the amplifier. Additionally, an electronic switch is connected in series with the integrating capacitor and opens/closes on command from the microprocessor. During integration, the switch is open for the integration and subsequent voltage measurement by an A-D converter. After integration and measurement, the switch is closed momentarily to discharge the capacitor and then reopened. A second measurement is now taken of the integrator output while the flashlamp is off, thereby giving a measure of the dark current and noise of the uv photodetector. This integrated dark current measurement is subtracted from the integrated signal to get a value for the true optical signal; the subtraction is done for both active and reference channels.

It is a principal object of the present invention to provide an ultraviolet point gas detection apparatus to check for unsafe levels of toxic gases.

It is another object of the present invention to provide a fail-to-safe toxic gas point detector, which will communicate to the user its detailed operational status.

Another object of the present invention is to provide a toxic gas point detector which does not require frequent and routine field calibration.

A further object of the present invention to provide a toxic gas point detection apparatus capable of operating in environments with oxygen deficiency or enrichment, and which is immune to poisoning by chemicals and vapors.

These and other advantages of the invention will become apparent from the following description and drawings.

BRIEF DESCRIPTION OF THE DRAWING

These and other features and advantages of the present invention will become more apparent from the following detailed description of an exemplary embodiment thereof, as illustrated in the accompanying drawings, in which:

FIG. 2 shows the electrical connection diagram of the ultraviolet toxic gas point detector.

FIG. 3 illustrates the timing of the various control and analog signals used in the ultraviolet toxic gas point detector.

DETAILED DESCRIPTION OF THE PREFERRED EMBODIMENT

Figure 1:
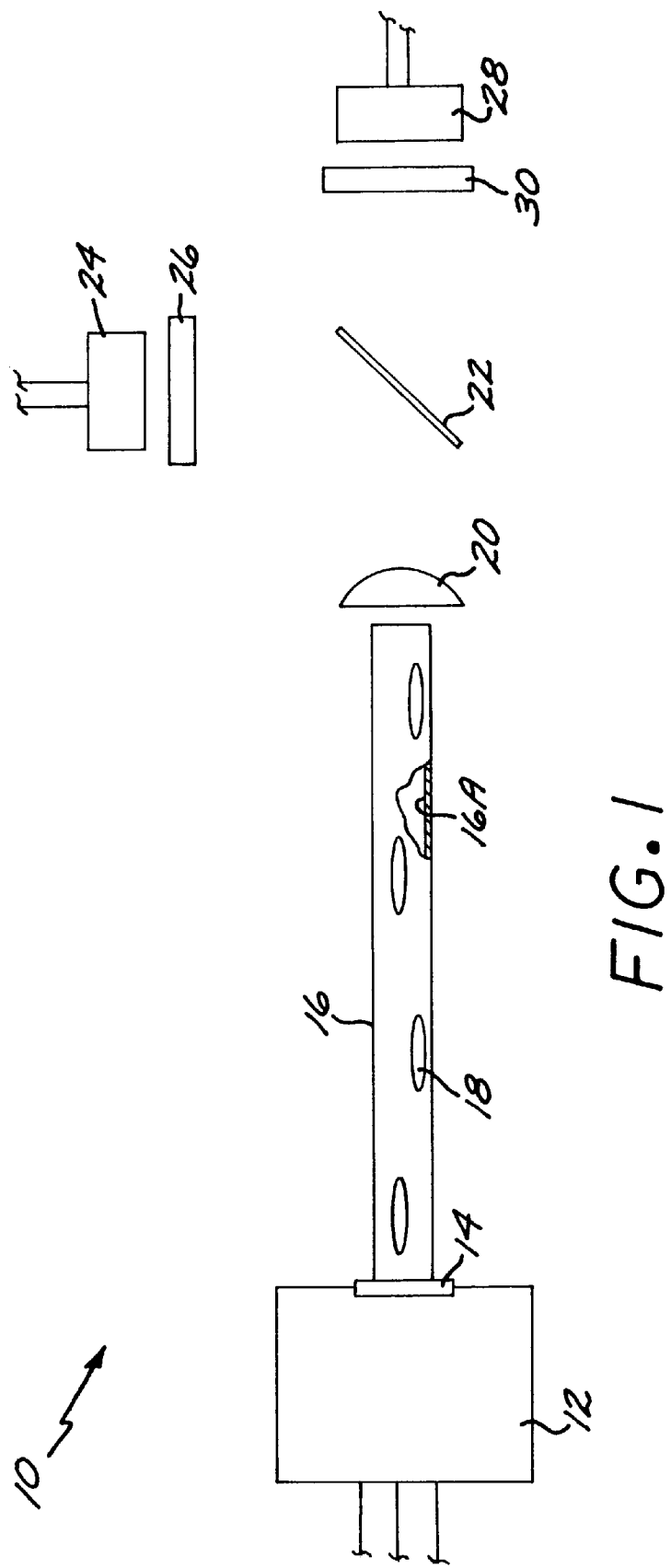
FIG. 1 is a diagrammatic cross-section of the optical elements of an ultraviolet toxic gas point detector embodying the features of the invention.

Referring first to FIG. 1, the optical components of an ultraviolet toxic point detector 10 in accordance with this invention are shown. The detector 10 comprises a xenon flashlamp 12 with an ultraviolet transparent window 14 made of material such as fused silica or magnesium fluoride. The ultraviolet radiation is coupled into a metal tube 16, which is several inches long and made of ultraviolet reflecting metal such as aluminum. The inside of this tube is highly polished by mechanical means and contains a number of perforations 18 along its length and around the circumference. The inside of the tube can also (optionally) be plated with other reflecting material coating 16A such as nickel. The purpose of the tube 16 is twofold. First, the tube collects ultraviolet radiation from the flashlamp source and efficiently guides it to the detecting element. Second, the number and size of holes in the tube 16 allow the absorbing gas to enter into the optical path.

After passing through the metal tube 16, the ultraviolet radiation, which is now fairly collimated by the tube, is collected and focused by a lens 20. The lens 20 is made of ultraviolet transmitting material such as fused silica, and may be a plano-convex f/2 lens with 1 inch focal length, for this exemplary embodiment. The focusing beam emerging from the lens is divided into two perpendicular beams by an ultraviolet beamsplitter 22. The beamsplitter is a flat silica plate, nominally 0.040 inch thick, with an optical coating. The coating of suitable dielectric or metal optimizes the reflectance of the beamsplitter at the active wavelength of 198 nm, and optimizes its transmittance at the reference wavelength of 280 nm. The coating can be also designed for other active and reference wavelengths in the ultraviolet using coating materials and thickness known to the optical coating industry.

The uv radiation reflected by the beamsplitter focuses onto a uv-enhanced silicon photodetector 24, in front of which is mounted the active filter 26 with center wavelength at 198 nm and a full width at half maximum (FWHM) bandpass of 25 nm. The uv radiation transmitted by the beamsplitter similarly focuses onto a second uv-enhanced photodetector 28, in front of which is mounted the reference filter 30 with center wavelength of 280 nm and a FWHM of 20 nm. These filters can also be mounted inside the covers of the photodetectors, in place of the uv transmitting windows which are integral to such photodetectors. Other filter center wavelengths and pass bands in the ultraviolet may also be used depending on the gas to be detected, within the scope of this invention.

FIG. 2 shows an exemplary electrical schematic of the electrical components of the detector 10. The uv flashlamp source 12 is powered by a power supply 34 and the discharge itself triggered by a trigger source 36. The timing of the trigger is set by the microprocessor 38 which provides the control timings for the entire instrument. The detector circuit 40, for each active and reference detector 24 and 28, includes an integrating capacitor 42 and electronic switch 44. The operational amplifier 42A and the capacitor 42 form an integrating amplifier. The switch 44 provides a low impedance path to discharge the capacitor. The signals from the detector are amplified by a gain stage 46, and then converted into digital levels by an analog to digital (A to D) converter 48. The digital levels are analyzed by the microprocessor 38, which performs calculations to be described below, and outputs a gas concentration value 50 using a calibration lookup table. The instrument also compensates for changes caused by temperature, the temperature being measured by a temperature sensor 52 integral to the instrument; the output of the temperature sensor is also converted into digital levels, and provided to the microprocessor. The gas concentration value 50 is outputted using a 4-20 mA or RS-485 serial communication link.

FIG. 3 shows the timing diagram of the instrument 10. The flashlamp 12 is discharged using the trigger 36 (A) which trigger is repeated at 5 to 10 Hz to provide continuous optical monitoring for the toxic gas. The optical flash (B) is integrated by the detectors using the capacitors 42 (C). After the flash is integrated, the same capacitor holds the integrated signal while it is measured (D) via the A/D converter 48. The integrator is then reset (E) using the switch 44. Since the flashlamp is now off, only dark current flows through the two detectors. This dark current is integrated (F) by reopening the switch 44. The integrated dark current is then measured (G). The acquired data consisting of the two optical integrated signals and the two integrated dark currents is now processed (H). The processing subtracts the integrated dark currents from the integrated optical signals for both channels, which subtraction removes the noise and drift from the measurement and provides a true optical signal. After the data processing, the gas concentration reading calculated from the measured signals is outputted (I). The whole cycle repeats itself after the microprocessor completes other house keeping tasks (J).

The gas concentration is derived from the following four electrical signals.

a) Active channel optical signal, $S_{ao}$
b) Active channel dark signal, $S_{ad}$
c) Reference channel optical signal, $S_{ro}$
d) Reference channel dark signal, $S_{rd}$ The active optical signal minus the active dark signal, $S_{ao}-S_{ad}$, gives the active signal proportional to the toxic gas absorption. The reference optical signal minus the reference dark signal, $S_{ro}-S_{rd}$, gives the reference signal proportional to the optical output of the flashlamp. Since the flashlamp output may vary over time, a true measure of the toxic gas concentration is obtained by scaling the active signal to the reference signal.

$$\text{Concentration } C=F([S_{ao}-S_{ad}]/[S_{ro}-S_{rd}]) \quad \text{(eq-1)}$$

where F is the function that relates the signal to the gas concentration through a lookup table 38A. The lookup table is determined at the factory by experimental measurements in this embodiment, and based on the Beer-Lambert Law relating absorption (or transmittance) to concentration. According to this Law, the transmitted intensity $I_t$ is related to the incident intensity $I_o$ by $$I_t=I_o\exp[-aCd] \quad \text{(eq. 2)}$$

where C is the concentration of absorbing gas, d the path length which equals the tube length and a is the absorption coefficient which is fixed for the gas at the particular wavelength. The difference between the incident intensity $I_o$ and the transmitted intensity $I_t$ gives the amount absorbed. Factory calibration essentially consists in fitting measured data to this curve, which curve is then stored in the microprocessor memory 38A.

The temperature of the gas detector, T °C, is measured by the sensor 52. Since the various components of the gas detector may have some (known and repeatable) temperature sensitivity, the function F may need to be corrected for the actual temperature T through a temperature function F(T), i.e.

$$C=F([S_{ao}-S_{ad}]/[S_{ro}-S_{rd}], T) \quad \text{(eq. 3)}$$

In accordance with another aspect of the invention, a method is provided for detecting the presence of parts per million levels of toxic gases in a fixed location by their ultraviolet absorption properties. In an exemplary embodiment, the method includes the following steps:

operating an ultraviolet light source to provide flashes of ultraviolet light;

guiding the flashes of light through a hollow tube having several perforations along its length to permit entry of the gas whose presence is to be detected;

separating the ultraviolet radiation guided by the tube into first and second beams;

directing the first beam through a first ultraviolet bandpass filter onto an active ultraviolet sensitive detector, the first filter tuned to a wavelength which is absorbed by the gas;

directing the second beam through a second ultraviolet bandpass filter onto a reference ultraviolet sensitive detector, the second filter tuned to a wavelength which is not absorbed by the gas;

operating the active and reference detectors during a first interval when light from the pulsed light source is incident on the detectors to make a first set of measurements when light is incident on the detectors and during a second interval when light from the pulsed light source is not incident on the detectors to make a second set of measurements; and processing the two sets of measurements to provide an output signal representative of the measured gas concentration.

The ability to track variations in the optical throughput of the lamp through the reference channel, and the inherent stability and immunity of optical gas detectors to chemicals and vapors, permit operation in the field free of routine and frequent calibration. Further, the availability of the reference channel signal provides for fail-to-safe operation since the sensor provides information on its active status, in contrast to chemical-type sensors whose status may not be determined without applying a reference gas.

The operation of optical detectors also does not require the presence of oxygen; further the operation does not suffer in presence of an oxygen rich atmosphere. Several types of existing sensors such as catalytic beads which operate on the principle of gas combustion are limited in operation to a narrow range of oxygen concentrations. Optical gas detectors operate on optical absorption principles which are independent of oxygen. The components of an optical gas detector such as source, detector and optics are also inherently more stable than the sensor elements used in chemical sensors.

It is understood that the above-described embodiments are merely illustrative of the possible specific embodiments which may represent principles of the present invention. Other arrangements may readily be devised in accordance with these principles by those skilled in the art without departing from the scope and spirit of the invention.

What is claimed is:

1. An optical gas detection apparatus with ability to detect the presence of toxic gases in a fixed location by their ultraviolet absorption properties, comprising:

an ultraviolet light source;

a hollow tube for guiding light emitted by the light source, said tube having several perforations along its length to permit entry of the absorbing gas whose presence is to be detected;

an ultraviolet beamsplitter which separates the ultraviolet radiation guided by the tube into two beams; and first and second ultraviolet sensitive detectors, said first detector sensitive to an ultraviolet wavelength which is absorbed by the gas, said second detector sensitive to an ultraviolet wavelength not absorbed by the gas, wherein the toxic gases have ultraviolet absorption in the 190 nm to 230 nm range, and wherein said first detector is sensitive to wavelengths in the range between 190 nm and 230 nm.

2. The apparatus of claim 1 further comprising an optical focusing element for focussing the ultraviolet radiation guided by the tube onto the beamsplitter.

3. The apparatus of claim 1, wherein the first and second ultraviolet detectors are uv-enhanced silicon photodetectors.

4. The apparatus of claim 1, wherein the light guiding tube has an internal surface which is highly reflective to ultraviolet radiation.

5. The apparatus of claim 1 wherein said light source is a pulsed flash lamp triggered by a trigger signal, and said apparatus further includes a controller for generating said trigger signal and controlling the operation of the apparatus.

6. The apparatus of claim 5 wherein said first detector provides an active output signal, and said second detector provides a reference output signal.

7. The apparatus of claim 6 wherein said controller is adapted to process said active output signals and said reference output signals to provide an apparatus output signal representative of a measured gas concentration.

8. The apparatus of claim 1 further comprising:
   a controller for receiving first detector output signals and second detector output signals, processing said output signals to provide an apparatus output signal representative of a measured gas concentration;
   a temperature sensor for sensing a temperature of said apparatus and providing a temperature signal representative of said sensed temperature; and
      wherein said controller is responsive to said temperature signal to compensate said apparatus output signal in dependence on said sensed temperature.

9. The apparatus of claim 1 wherein the toxic gases do not absorb ultraviolet radiation at 280 nm, and said second detector is sensitive to ultraviolet radiation at 280 nm.

10. The apparatus of claim 9 further including a first ultraviolet optical filter in an optical path between the beamsplitter and the first detector, wherein the first filter is a narrow-band filter having a pass band for passing only radiation in an absorption range of the toxic gases, and a second ultraviolet optical filter in an optical path between the beamsplitter and the second detector, wherein the second filter is a narrow-band filter having a pass band for passing only ultraviolet radiation in a range which is not absorbed by the toxic gases.

11. The apparatus of claim 10 wherein said pass band of said first filter is centered at 198 nm, and said pass band of said second filter is centered at 280 nm.

12. The apparatus of claim 1 wherein the toxic gases include hydrogen sulfide, sulfur dioxide, benzene, toluene and zylene.

13. A method for detecting the presence of parts per million levels of toxic gases in a fixed location by their ultraviolet absorption properties, comprising a sequence of the following steps:
   operating an ultraviolet light source to provide flashes of ultraviolet light;
   guiding the flashes of light through a hollow tube having several perforations along its length to permit entry of the gas whose presence is to be detected;
   separating the ultraviolet radiation guided by the tube into first and second beams;
   directing the first beam through a first ultraviolet bandpass filter onto an active ultraviolet sensitive detector, said first filter tuned to an ultraviolet wavelength which is absorbed by the gas;
   directing the second beam through a second ultraviolet bandpass filter onto a reference ultraviolet sensitive detector, said second filter tuned to an ultraviolet wavelength which is not absorbed by the gas;
   operating the active and reference detectors during a first interval when light from the pulsed light source is incident on the detectors to make a first set of measurements when light is incident on said detectors and during a second interval when light from the pulsed light source is not incident on the detectors to make a second set of measurements; and
   processing the two sets of measurements to provide an output signal representative of the measured gas concentration.

14. The method of claim 13, further characterized in that each of said steps is carried out in an atmosphere deficient in oxygen.

15. The method of claim 13, further characterized in that each of said steps is carried out in an oxygen-enriched atmosphere.

16. The method of claim 13, further characterized in that an accuracy of said output signal is immune to poisoning by chemicals and vapors.

17. The method of claim 13 wherein the first bandpass filter through which the first beam is directed is tuned to a wavelength in the range of 190 nm to 230 nm.

18. The method of claim 17 wherein the second bandpass filter through which the second beam is directed is tuned to 280 nm.

19. The method of claim 13 wherein the toxic gases include hydrogen sulfide, sulfur dioxide, benzene, toluene and zylene.

20. An optical gas detection apparatus with ability to detect the presence of parts per million levels of toxic gases in a fixed location by their ultraviolet absorption properties, comprising:
   an ultraviolet flashlamp with an ultraviolet transmitting window;
   a highly polished metal tube which acts as a light guide and contains several perforations along its length to permit entry of the toxic gas;
   an optical focusing element;
   an ultraviolet beamsplitter which separates the ultraviolet radiation into two mutually perpendicular beams; and
   a pair of ultraviolet sensitive detectors with ultraviolet bandpass filters, one filter at a first ultraviolet wavelength which is absorbed by the toxic gas, with the second filter at a second ultraviolet wavelength not absorbed by the toxic gas.

21. The apparatus of claim 20, wherein the ultraviolet detectors are uv-enhanced silicon photodetectors.

22. The apparatus of claim 21, wherein the ultraviolet filters are mounted external to the ultraviolet detectors.

23. The apparatus of claim 21, wherein the ultraviolet filters are mounted internal to the ultraviolet detectors, being integral to the covers of the detectors.

24. The apparatus of claim 20, wherein the metal light guide tube includes a highly polished internal surface.

25. The apparatus of claim 20, wherein the metal light guide tube is plated with an ultraviolet reflecting material.

26. The apparatus of claim 20 wherein said one filter is tuned to a wavelength in the range of 190 nm to 230 nm.

27. The apparatus of claim 26 wherein said second filter is tuned to 280 nm.

28. The apparatus of claim 20 wherein the toxic gases include hydrogen sulfide, sulfur dioxide, benzene, toluene and zylene.

29. An optical gas detection apparatus with ability to detect the presence of parts per million levels of toxic gases in a fixed location by their ultraviolet absorption properties, comprising:
   an ultraviolet flashlamp with an ultraviolet transmitting window;
   a highly polished metal tube which acts as a light guide and contains several perforations along its length to permit entry of the toxic gas;
   an optical focusing element;
   an ultraviolet beamsplitter which separates the ultraviolet radiation into two mutually perpendicular beams; and
   a pair of ultraviolet sensitive detectors with ultraviolet bandpass filters attached, one filter at a wavelength which is absorbed by the toxic gas, with the second filter at a wavelength not absorbed by the toxic gas, wherein said one ultraviolet filter is centered at 198 nm, and said second filter is centered at 280 nm.

* * * * *